US008617074B2

United States Patent
De Korte (10) Patent No.: US 8,617,074 B2
(45) Date of Patent: Dec. 31, 2013

(54) METHOD AND APPARATUS FOR GENERATING HARDNESS AND/OR STRAIN INFORMATION OF A TISSUE

(75) Inventor: Christoffel Leendert De Korte, Driebergen (NL)

(73) Assignee: Stichting Katholieke Universiteit, Nijmegen (NL)

( * ) Notice: Subject to any disclaimer, the term of this patent is extended or adjusted under 35 U.S.C. 154(b) by 653 days.

(21) Appl. No.: 11/990,543

(22) PCT Filed: Aug. 18, 2006

(86) PCT No.: PCT/NL2006/000429
§ 371 (c)(1),
(2), (4) Date: Jun. 12, 2008

(87) PCT Pub. No.: WO2007/021185
PCT Pub. Date: Feb. 22, 2007

(65) Prior Publication Data
US 2009/0099447 A1    Apr. 16, 2009

Related U.S. Application Data

(60) Provisional application No. 60/708,879, filed on Aug. 18, 2005.

(51) Int. Cl.
*A61B 8/00* (2006.01)

(52) U.S. Cl.
USPC ........... 600/438; 600/437; 600/443; 600/444; 600/445

(58) Field of Classification Search
USPC ........... 600/438, 442, 450, 443–445; 442/262
See application file for complete search history.

(56) References Cited

U.S. PATENT DOCUMENTS 5,411,028 A * 5/1995 Bonnefous .................... 600/454
5,928,151 A * 7/1999 Hossack et al. ............... 600/443
(Continued)

FOREIGN PATENT DOCUMENTS

| EP | 0 908 137 A1 | 4/1999 |
| EP | 1 529 491 A1 | 5/2005 |
| WO | WO 03/017845 A1 | 3/2003 |

OTHER PUBLICATIONS

Konofagou, Elisa et al., "A New Elastographic Method for Estimation and Imaging of Lateral Displacements, Lateral Strains, Corrected Axial Strains and Poisson's Ratios in Tissues," Ultrasound in Med. & Biol., vol. 24, No. 8, pp. 1183-1199, 1998.

(Continued)

*Primary Examiner* — Long V. Le
*Assistant Examiner* — Farshad Negarestan
(74) *Attorney, Agent, or Firm* — Preti Flaherty Beliveau & Pachios LLP (57) ABSTRACT

The invention is related to a method for generating hardness and/or strain information of a tissue which can be subject to a varying pressure, the method comprising: —positioning at least one signal transmitter (1) outside the tissue (10); —positioning at least one signal receiver (1) outside the tissue (10); —using the signal transmitter (1) to send signals (S) at different angles towards the tissue; —using the signal receiver (1) to receive signals from the tissue (10), wherein the received signals result from the signals that have been sent by said signal transmitter. The invention is also related to an apparatus for carrying out the method.

13 Claims, 4 Drawing Sheets

(56) References Cited

U.S. PATENT DOCUMENTS

| | | | |
|---|---|---|---|
| 6,468,215 B1* | 10/2002 | Sarvazyan et al. | 600/438 |
| 7,404,798 B2* | 7/2008 | Kato et al. | 600/450 |
| 2004/0009459 A1* | 1/2004 | Anderson et al. | 434/262 |
| 2004/0215075 A1* | 10/2004 | Zagzebski et al. | 600/442 |
| 2007/0282202 A1* | 12/2007 | Maurice et al. | 600/438 |

OTHER PUBLICATIONS

De Korte, Chris L., et al., "Influence of Catheter Position on Estimated Strain in Intravascular Elastography," IEEE Transactions on Ultrasonics, Ferroelectrics, and Frequency Control., vol. 46, No. 3, May 1999, pp. 616-625.

* cited by examiner

METHOD AND APPARATUS FOR GENERATING HARDNESS AND/OR STRAIN INFORMATION OF A TISSUE

This application is a §371 national phase filing of PCT/NL2006/000429 filed Aug. 18, 2006, and claims priority to U.S. Prov. Appln. No. 60/708,879 filed Aug. 18, 2005.

The invention relates to a method and apparatus, which can be used for generating deformation and/or hardness information of tissue, for example a circular (or cylindrical) tissue subject. In particular, the method relates to a method for generating hardness information of the wall of a blood vessel or body cavity.

Such a method is known from European application EP-A 0 908 137. In this application, the strain (deformation) of the vessel walls is derived with ultrasound from the relative displacement of a more inward layer and a more outward layer of the vessel wall as a result of the varying intra vessel pressure through the heartbeat. These relative displacements are (at an assumed equal speed of sound in the medium) equal to the difference of relative time delays of the ultrasound beam, measured at two or more times.

The relative time delay can be measured by correlating with each other sound signals obtained consecutively over time from one specific direction and deriving the relevant time delay from a correlation optimum. This optimum occurs when the time difference between the respective signals is equal to the relevant time delay. By taking the difference of time delays measured at two different echo depths along the measuring beam and relating this to the time difference between these echo depths, it is possible to derive the degree of strain of the vessel wall in the direction of the sound beam as a result of pressure changes induced by the heartbeat. By measuring several relative displacements along the measuring beam, it is possible to derive the degree of strain in different areas of the vessel wall in the direction of the sound beam as a result of pressure changes induced by the heartbeat. By measuring the local relative displacements with a measuring beam in a specific direction and performing this measurement in a measuring plane oriented transversely to the vessel wall, it is possible to display elasticity information about respective measuring positions in the measuring plane, a so-called elastogram. By measuring only one strain value per measuring beam corresponding to the layer at the lumen-tissue boundary and superimposing this information on the conventional echo-image as a color coded contour at the lumen-tissue boundary a so-called palpogram is generated. The information derivable form such an elastogram/palpogram is important to identify and characterize plaques on the vessel walls. The composition of plaques can be important to the assessment of the injuriousness to health.

Such information is often not derivable from a conventional echogram, since the image of high-risk plaques cannot be distinguished from less high-risk plaques. Moreover, practical and theoretical studies show that the degree of strain of the vessel wall is indicative of the stresses that can occur in such plaques. If stresses become too high, a plaque can tear open, so that a life threatening thrombosis can arise.

A satisfactory image of the strain can be generated by inserting a transducer (a combination of a transmitter and receiver) in the lumen of the vessel, see for example WO 03/017845A1, the content of which is incorporated in the present application in its entirety. In a vessel wall, the interesting strain of tissue is primarily from the lumen vessel wall boundary to outside (radial strain) and perpendicular to the radial strain (circumferential strain). If the transducer is positioned in the lumen, the direction of the measuring beam and the radial strain are aligned. Consequently, a proper estimate of this component of the strain can be obtained. Using lateral strain estimation methods as disclosed in an article in Ultrasound in Medicine and Biology, vol. 24(8), pp 1183-1199, 1998, the circumferential strain in the vessel wall can be determined.

However, it is not always desirable to insert a transducer in the lumen of a vessel. Preferably, vessels are visualized from outside the body. However, it has been found that it is difficult to obtain a complete strain image of the tissue using non-invasive techniques since the radial strain and the measuring beam are not aligned, see for example theoretical studies as disclosed in an article in IEEE Transactions on Ultrasonics, Ferroelectrics and Frequency Control, vol. 46(3), pp. 616-625, 1999.

The present invention aims to provide an improved method and an improved apparatus for strain estimation and/or hardness imaging of tissue or tissue structures, for example tissue structures having substantially circular cross-sections such as blood vessels or similar tissue.

According to an embodiment of the invention, a method for generating hardness and/or strain information of a tissue which can be subject to a varying pressure, comprises:

positioning at least one signal transmitter outside the tissue, for example outside a body which includes the tissue;

positioning at least one signal receiver outside the tissue, for example outside a body which includes the tissue;

using the signal transmitter to send signals at different angles towards the tissue;

using the signal receiver to receive signals from the tissue, wherein the received signals result from the signals that have been sent by said signal transmitter, for example due to said tissue at least partly reflecting those signals.

For example, in an embodiment of the invention, this invention uses steering of measuring beams (sent by the signal receiver) over multiple angles, with respect to the tissue, and detecting resulting reflected signal parts.

Also, in an embodiment, the mentioned transmitter and receiver can be integrated with each other, or be provided by a single component or device, for example in the case a suitable signal transducer is applied.

For non-invasive assessment of the geometry of carotid arteries with ultrasound, linear array transducers can be used. Using a linear array transducer, ultrasound (measuring) beams can not only be emitted perpendicular to the transducer surface (an angle of 90 degrees), from that surface, but also under smaller angles (down to 45 degrees). Therefore, images of the carotid artery can be made under different angles. In this way, regions where no strain can be determined are at other positions for the images acquired at different angles. Compounding of these images can result in a full reconstruction of the radial and circumferential strain for all regions of the vessel wall.

According to an embodiment of the invention, there is provided an apparatus for generating hardness and/or strain information of a tissue, for example specifically adapted to carry out a method according to the invention, wherein the apparatus comprises:

at least one signal transmitter which is configured to be located outside a tissue during use to transmit at least one signal towards the tissue; and at least one signal receiver which is configured to be located outside the tissue during use, to receive signals from the tissue;

wherein the transmitter is arranged to generate signals having different directions of propagation.

For example, according to an embodiment, the signal transmitter can be arranged to send signals in a first direction which encloses at least a first angle with a surface of the signal transmitter, wherein the signal transmitter is also arranged to send signals in a second direction which encloses at least a second angle (differing from the first angle) with the surface of the signal transmitter. Said first angle and said second angle can differ, for example, about 25 to 65 degrees with each other, for example about 35 to 55 degrees, particularly for example about 45 degrees. Also, said first angle can be, for example, in the range of about 80-100 degrees, for example about 90 degrees. Also, said second angle can be, for example, in the range of about 25-65 degrees, for example about 35 to 55 degrees, particularly for example about 45 degrees.

Further advantageous embodiments of the invention are described in the dependent claims.

The invention will be further explained by non-limiting examples on the basis of the description of the drawings in which.

In the present application, similar or corresponding features are denoted by similar or corresponding reference signs.

Figure 1A:
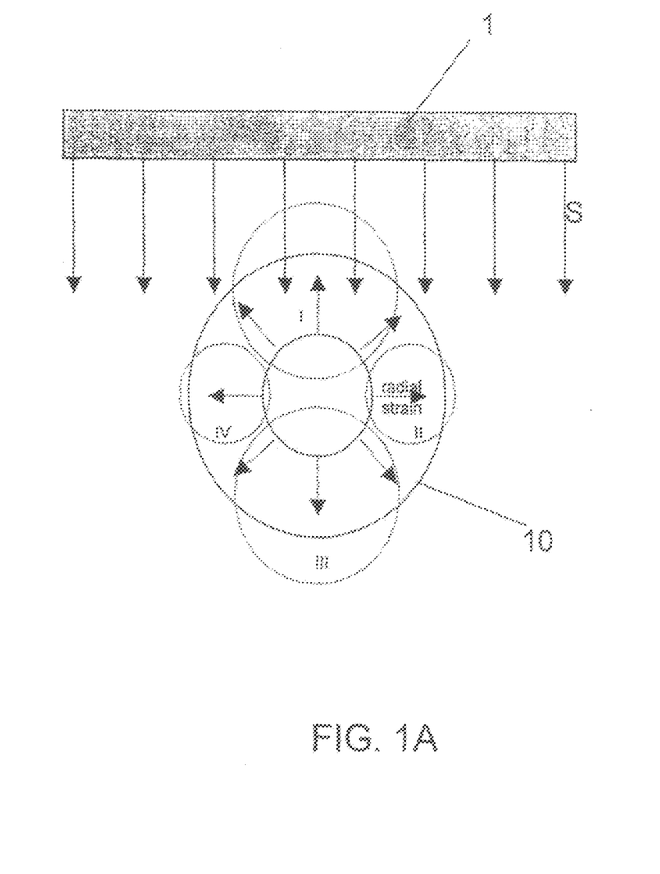
FIGS. 1A, 1B schematically depict a method according to a first embodiment of the invention.

FIG. 1A depicts the application of a transducer 1 to emit a measuring beam (or a beam of a plurality of measuring signals) S towards a circular (or cylindrical) tissue 10. For example, the measuring beams/signals S can be ultrasound beams. The measuring beams S can be emitted, for example, by a transmitter of a suitable transducer 1, for example a linear array transducer 1. The transducer 1 can also be configured to detect signals that are reflected back towards the transducer 1 by the tissue 10. As an example, the tissue can be a vessel wall of a blood vessel 10.

As is depicted in FIG. 1A, if the transducer 1 is not positioned in the lumen of the vessel wall of the blood vessel 10, the direction of the (for example ultrasound) beam S and the direction of the radial strain in the vessel wall are generally not aligned. The radial and circumferential components of the strain make an angle between −180 and +180 degrees with the measuring beam, depending on the location in the arterial wall.

In FIG. 1A, in region I and III (depicted by respective dotted circles in FIG. 1A), the angle between the measuring beam S and the radial strain in the vessel wall is small. In these regions, the radial strain in the vessel wall can be determined by calculating the strain in the direction of the measuring beam. In these regions, the circumferential strain in the vessel wall can be determined using lateral strain estimation techniques. In regions II and IV (also depicted by respective dotted circles in FIG. 1A), the angle between the measuring beam S and the circumferential strain in the vessel wall is small. In these regions, the circumferential strain in the vessel wall can be determined by calculating the strain in the direction of the measuring beam. In these regions, the radial strain in the vessel wall can be calculated by using lateral strain estimation techniques.

For example, in FIG. 1A, in the locations between regions I, II, III and IV, the angle between the radial strain and the measuring beam can be around 45 and 75 degrees, or for example circa 50 and 70 degrees (see FIG. 1A).

Figure 1B:
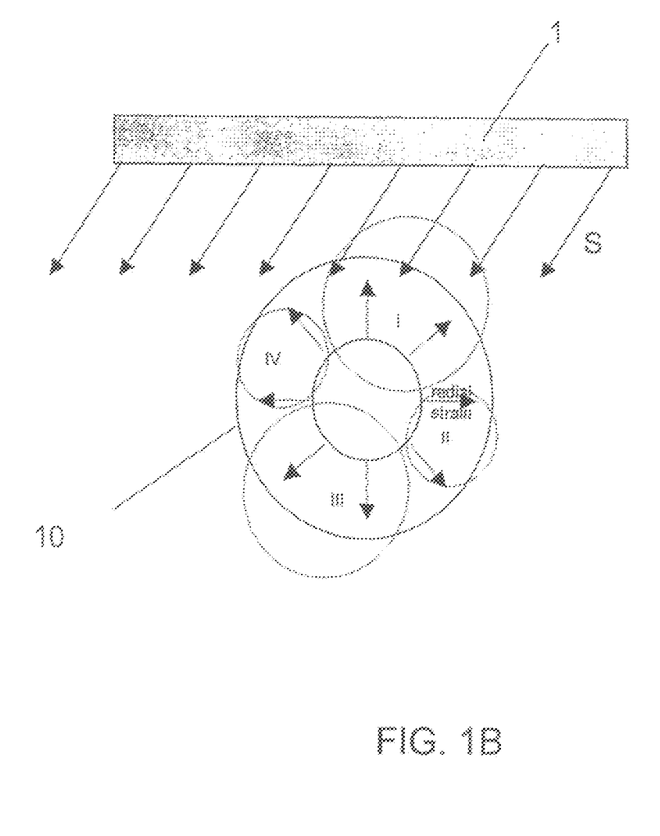

Particularly, FIGS. 1A-1B are a schematic representation of a method according to the invention, to acquire data of a circular tissue structure, i.e. a structure 10 having a circular cross-section, using subsequent different imaging planes. In this case, the different imaging planes are composed of or provided by measuring beams S, or a plurality of signals S that are or run parallel in a particular image plane (see FIGS. 1A and 1B). For example, the angle between the measuring beams and the transducer surface is different for the different imaging planes (compare FIGS. 1A and 1B). Therefore, a plurality of signals is first being sent in a first direction which encloses at least a first angle with a surface of the signal transmitter (which is shown in FIG. 1A), and after that in a second direction which encloses at least a second angle (different from the first angle) with the signal transmitter (see FIG. 1B). Thus, various outer surface parts of the tissue 10 (which surface parts can be reached by the beam emanating from the transducer 1) receive the measuring beam subsequently with different angles of incidence.

As will be appreciated by the skilled person, each plurality of signals S can be configured to determine strain in the tissue, which can be achieved by transmitting more than one signal in the same direction while the tissue under interrogation is at various levels of deformation. This is known as such from prior art ultrasound tissue elastography.

For example, the transmitting of the signals in the first direction can include: transmitting at least one signal towards the tissue while the tissue is at a certain (first) level of deformation (in the first direction) and shortly thereafter transmitting at least one signal towards the tissue while the tissue is at a different level (i.e. different from the first level) of deformation (also in the first direction). In the same way, the transmitting of the signals in the second direction can include: transmitting at least one signal towards the tissue while the tissue is at a certain level of deformation (in the second direction) and shortly thereafter transmitting at least one signal towards the tissue while the tissue is at a different level of deformation (in the second direction). Thus, each step of sending of signals in a certain direction can involve a short time period, in which at least two signals are being sent after each other while the tissue is deforming.

In FIG. 1A, the transducer 1 is positioned outside the tissue 10, and sends a plurality of signals S in a first direction which encloses at least a first angle with a surface of the transducer (or signal transmitter). After the transmission of the signals in the first direction, the transducer 1 sends signals in a second direction (see FIG. 1b) which encloses at least a second angle with the transducer 1. Herein, the positioning of the transducer 1 with respect of the tissue 10 remains unaltered. Thus, in FIG. 1, the transducer 1 is configured to subsequently generate signals having different directions of propagation, i.e., different with respect to the transducer 1. From FIGS. 1A, 1B it clearly follows, that the transducer can be configured and dimensioned such, that at least part of the transmitted signals can reach the tissue 10, in case of sending signals at the first angle as well as the second angle. Herein, for example, the width of the transducer can depend on the width of the tissue as well as on the distance between transducer and tissue. Clearly, a wider transducer can be provided in case the transducer is located further away from the tissue. For example, the width of the transducer (measured in FIG. 1A perpendicularly to the signals S and to the imaging plane) can be (significantly) larger than the width of the tissue 10 (measured in the same direction). Also, for example, as follows from FIG. 1A-1B, the transducer 1 can be positioned approximately centrally with respect to the tissue 10, opposite/outside the tissue 10, during operation.

The mentioned second angle differs from the first angle. For example, said first angle and said second angle can differ about 35 to 55 degrees with each other, for example about 45 degrees (see FIG. 1B). For example, said first angle can be in the range of about 80-100 degrees, for example about 90 degrees (as in FIG. 1A). Also, for example, said second angle can be in the range of about 25-65 degrees, for example about 35-55 degrees, particularly for example about 45 degrees. Signals, which result from said signals being sent to the tissue, for example reflections or echo's of those signals, are received by a receiver, which is also part of the transducer. For example, from echoes resulting from signals (that have been sent in a certain direction), tissue deformation can be determined, as will be appreciated by the skilled person. These echoes can be compared with each other to determine tissue deformation.

In an embodiment of the invention, by (for example electronically) steering the image plane of a linear array transducer, several images of the tissue with different angles between the transducer and the ultrasound signals can be acquired without moving the transducer with respect to the tissue or a body which contains the tissue.

In a first step (see FIG. 1A), signals from the tissue with a transducer 1 (particularly an acoustic transducer) positioned outside the tissue or tissue structure for measuring the deformation of the tissue 10 in a first measuring plane defined by the sensor in which the measuring beams as generated by the transmitter are all parallel and with a certain angle towards the transducer surface (see FIG. 1a). It has been found that in this first step, in regions where the angle between ultrasound beam and radial strain is around plus or minus 60 degrees, the strain cannot be determined.

Next, without moving the transducer with respect to the tissue, in a second step, signals S are generated by the transmitter 1 and received by the receiver 1 from the tissue for measuring deformation of the tissue 10 in a second measuring plane (or one or more other measuring planes) defined by the transducer 1, in which the measuring beams are parallel but with a different angle to the transducer surface than in the previous step (FIG. 1b). The difference in angle between the measuring beams of the first and the second step is preferably in the order of plus or minus 45 degrees. In this way, in regions were the angle between ultrasound beam and radial strain were around plus or minus 60 degrees in the above-mentioned first step (FIG. 1A), the strain can be determined using said second step. Consequently, a complete strain image will be generated. As mentioned above, each step of emitting signals S can involve emission of a plurality of signals to perform tissue deformation imaging.

For example, during use, the transmitter 1 can transmit subsequent signals S with time differences of about 100 ms or less.

In this way, the radial and circumferential strain can be assessed for all regions by combining the strain images acquired under the different angles used in said first and second step. Since this images can be acquired very fast after each other (time between images lower than 100 ms), this technique can be used for vascular applications (see FIG. 1). Also, the method can comprise the step of displaying elasticity and/or hardness parameters of the tissue. Also, the signals can be used to provide echographic data.

Figure 2A:
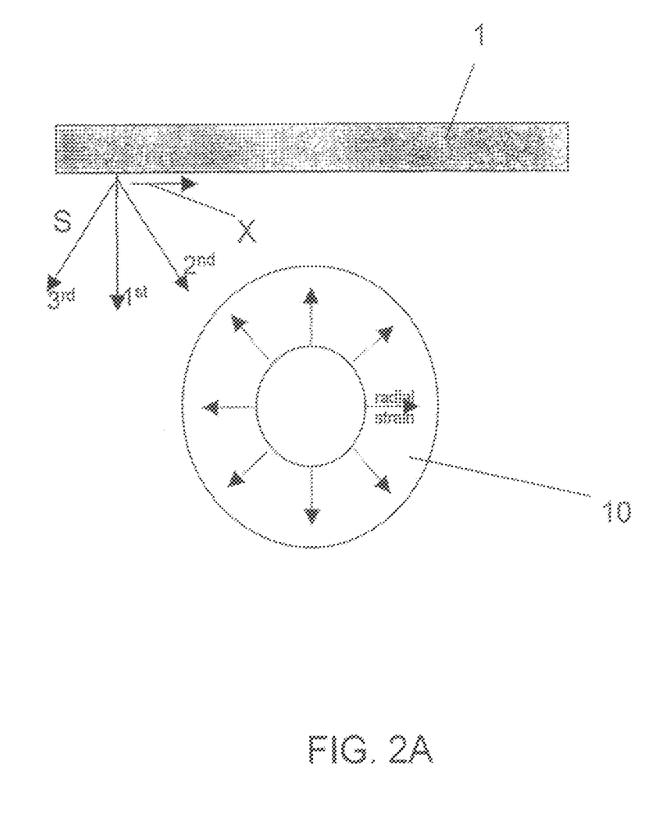
FIGS. 2A, 2B schematically depict a method according to a second embodiment of the invention.
Figure 2B:
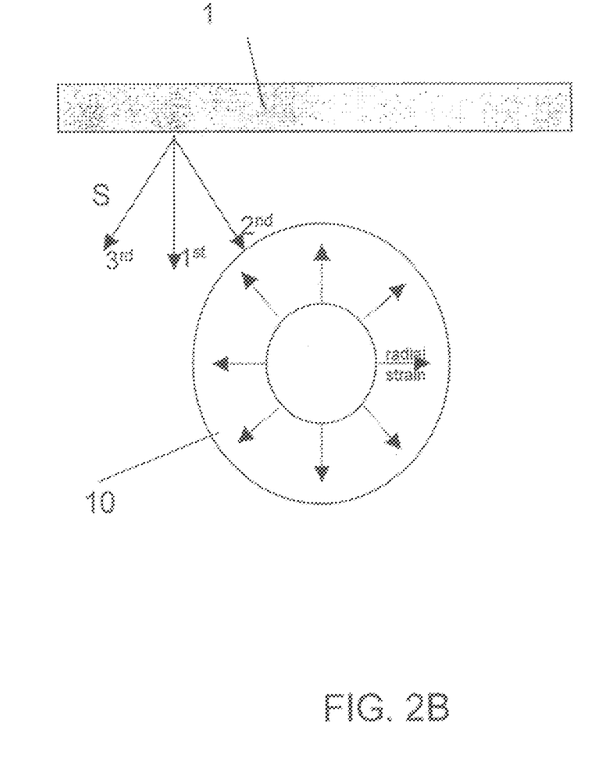

FIG. 2 is a schematic representation of an alternative method to acquire data of tissue structure 10 in which measuring beams S with different angles with respect to the transducer surface are being transmitted at the same time. In FIGS. 2A, 2B, only a first ($1^{st}$), second ($2^{nd}$) and third ($3^{rd}$) beam S are shown, however, a different number of measuring beams can also be emitted at the same time, at different angles. In this case, the beams S can originate from the same spot or location of the transducer or transducer surface (see FIG. 2). An image plane is formed by repeating this procedure (i.e. the emission of different beams—at different angles—at the same time) for measuring beams originating from different locations of the transducer. A shift of the location of emission of a group of measuring beams (towards the location shown in FIG. 2B) is indicated by an arrow X in FIG. 2A. As follows from the drawing, this shift leads to the beams S intersecting the tissue 10 at subsequently different angles.

In the embodiment of FIG. 2, for example, diverging measuring beams, or a group of diverging signals, can be sent to the tissue by the transducer 1, from subsequently different locations of the transducer or transducer surface. The signals, or parts thereof, that return from the tissue towards the transducer can be detected by the transducer. The diverging measuring beams can be arranged in several ways. For example, the diverging measuring beams can also include signals that enclose said first angles with the transducer surface, and signals that enclose said second angles with the transducer surface. Also, in this case, emission of each group of diverging signals can include at least two sub-emissions, shortly after each other, for tissue deformation imaging.

Thus, as in FIG. 2, it is also possible to steer separate ultrasound beams under different angles. In this way, two or more signals from the tissue are received with a transducer 1 positioned outside the tissue or tissue structure for measuring the deformation of the tissue in a measuring plane defined by the transducer in which the measuring beams have different angles towards the transducer surface but originate from the same location of the transducer. The difference in angle between the first signal and the other signals is preferably in the order of plus or minus 45 degrees (FIG. 2a). Next, without moving the transducer, two or more signals from the tissue for measuring the deformation of the tissue are received in a measuring plane defined by the transducer in which the measuring beams have different angles towards the transducer surface but all these beams originate from the same location of the transducer but this location is another location than the previous location. The difference in angle between the first signal and the other signals is preferably in the order of plus or minus 45 degrees.

Figure 3:
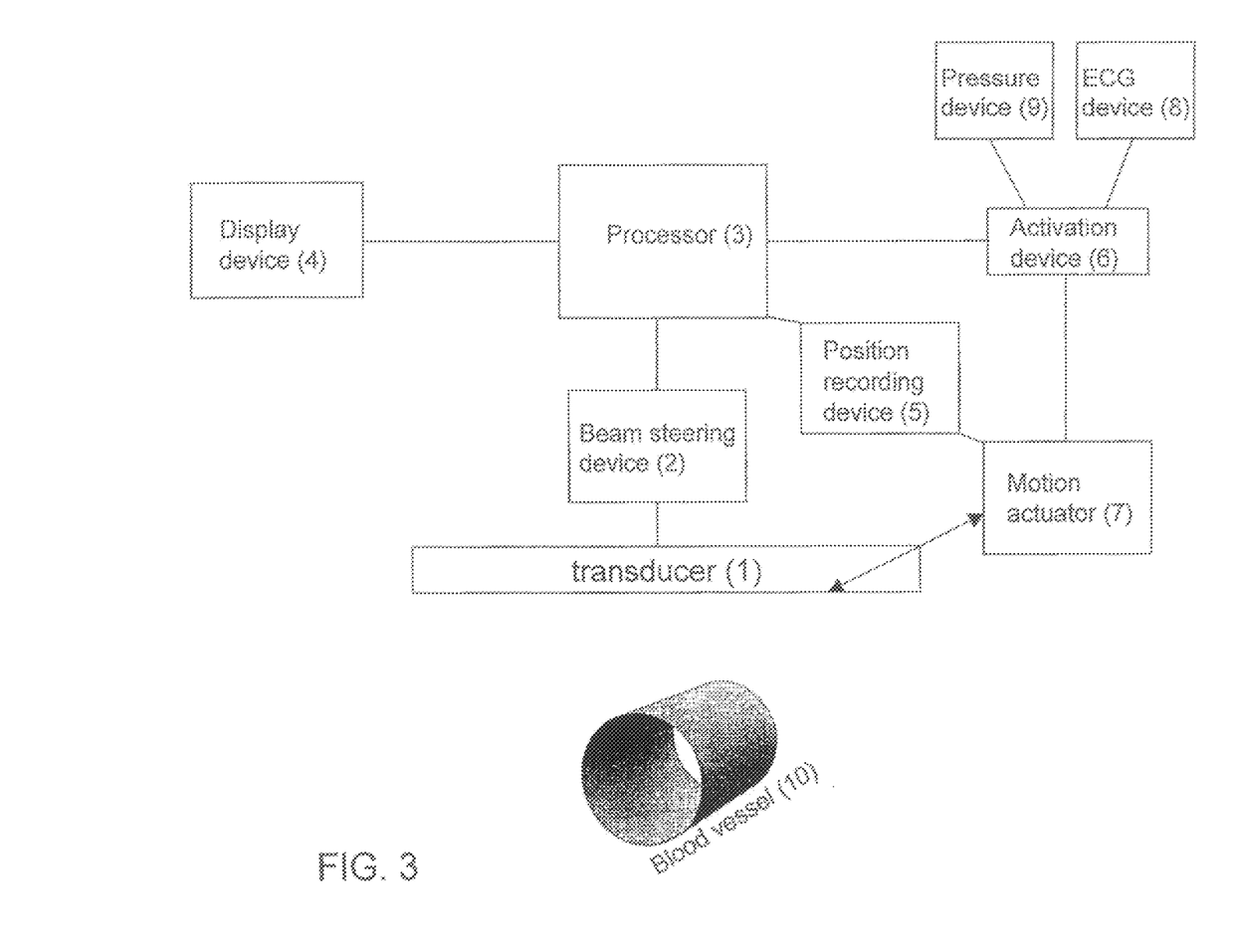
FIG. 3 schematically depicts an apparatus according to an embodiment of the invention.

FIG. 3 is a diagrammatic representation of an embodiment of an apparatus according to the invention, which can be used in the embodiments of FIGS. 1 and/or 2. This apparatus can comprise a linear array transducer 1, or another transducer, which can serve as a signal transmitter as well as a signal receiver. Ultrasound beams, that can be generated by this transducer, can be steered with different angles with respect to the transducer surface by the beam steering device 2 (see above). A processor 3 is present to collect and process the echographic data. Also, the apparatus can comprise a display device 4 for displaying elasticity and/or hardness parameters of the tissue. The processor 3 can be connected to the display device 4, which can be achieved in various ways as will be clear to the skilled person, for example by suitable communication means. Also, the apparatus can comprise a position recording device 5, which is preferably coupled with the processor device 3, to record positions of said transmitter and/or receiver with respect to said tissue 10. The transducer can be moved with respect to the blood vessel 10 by a motion actuator 7 that is controlled by an activation device 6. Particularly, the movement is parallel to the blood vessel 10, along the blood vessel, so that subsequent (axially neighbouring) blood vessel parts can be examined by the apparatus. Also, for example, the activator 6 can be configured to activate said signal transmitter to transmit said signal, and/or to activate said signal receiver to receive said signal.

Besides, in an embodiment, the apparatus can be arranged to be connected to an ECG recording device 8 and/or pressure monitoring device 9, preferably such that during use the apparatus becomes active during a predetermined part of the heartcycle.

During use of the apparatus, the acquisition of data can be limited to certain times in the pressure cycle. Using an ECG signal 8 or a signal generated by a device that continuously measures the blood pressure 9, data acquisition can be limited to certain parts of the pressure cycle. Furthermore, it is possible to acquire three dimensional information of the tissue by moving the transducer in a direction perpendicular to the initial imaging plane. If a motorized device 7 is used to move the transducer, movement of the transducer can be controlled using the ECG 8 or blood pressure signal 9.

In the present application, a multi-angle approach can be used to assess strain in regions of the vascular wall that are difficult to be assessed using one acquisition at a fixed angle only.

Figure 4:
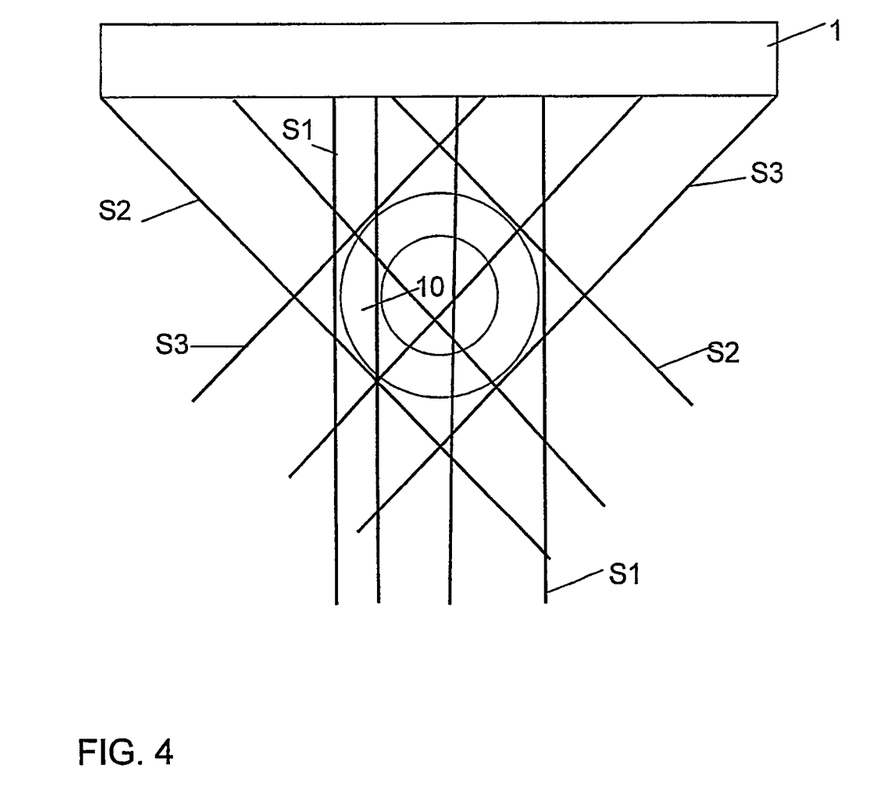
FIG. 4 schematically depicts an embodiment of the invention.

FIG. 4 shows an embodiment, similar to that of FIGS. 1A-1B, 2A-2B. In FIG. 4, a plurality of ultrasound signals S1 (four depicted, as an example) is emitted at an angle of about 90 degrees from a transducer 1 towards the tissue 10. Ultrasound signals S2 (three depicted) are emitted at an angle of about 45° from the transducer 1 towards the tissue 10. Ultrasound signals S3 (three depicted) are emitted at an angle of about −45 degrees from the transducer 1 towards the tissue 10. This embodiment can provide the above-mentioned advantages. As follows from FIG. 4 (and also from FIGS. 1-2), the transducer 1 can be positioned such and be dimensioned such, that each group of emitted signals S1, S2, S3 can encompass the contour (in cross-section) of the tissue 10 which is to be examined.

In the above, methods are described that are based on acoustic measuring beams generated and received by an ultrasound transducer. The method can also be performed using optical measuring signals or a combination of acoustical and optical signals. Furthermore, a method has been described using the pulsatile blood pressure as a source for deformation. This method can also be applied on tissues that are deformed by other sources than the blood pressures originating from inside the body (like breathing or active muscle contraction) or a by means of artificially exerting a pressure variation of the tissue.

Also, for example, according to another embodiment (see FIG. 1), there can be provided a method for generating strain and/or hardness information of a tissue or tissue structure which is or can be subject to a varying pressure, comprising the steps of:

1) receiving signals from the tissue with a sensor 1 positioned outside the tissue for measuring the deformation of the tissue in a measuring plane defined by the sensor 1 in which the measuring beams are all parallel and with a certain angle towards the sensor surface;

2) without moving the sensor, receiving the signals from the tissue for measuring deformation of the tissue in a measuring plane defined by the sensor 1 in which the measuring beams are parallel but with a different angle to the sensor surface than in the first step; herein, the angle with respect to the sensor surface between the first and the second step is preferably in the order of about 45 degrees;

Identifying the strain of the tissue by compounding the information acquired in step 1) and 2); and Relating the strain to elasticity and/or hardness parameters of the tissue.

Also, for example, a method for generating hardness information of a tissue subject to a varying pressure can comprise the steps of (see FIG. 2):

1) receiving two or more signals from the tissue with a sensor 1 positioned outside the tissue for measuring the deformation of the tissue in a measuring plane defined by the sensor in which the measuring beams have different angles towards the sensor surface but originate from the same location of the sensor; herein, the angle with respect to the sensor surface between the first signal and the other signals is preferably in the order of about 45 degrees;

2) Without moving the sensor 1, receiving two or more signals from the tissue for measuring the deformation of the tissue in a measuring plane defined by the sensor in which the measuring beams have different angles towards the sensor surface but originate from the same location of the sensor in which this location is another location; the angle with respect to the sensor surface between the first signal and the other signals is preferably in the order of about 45 degrees;

3) Repeating step 2 until an image is acquired; and

Identifying the strain of the tissue by compounding the information acquired in step 1, 2 and 3.

Relating the strain to elasticity and/or hardness parameters of the tissue.

Furthermore, as follows from the above, the method can comprise the step of displaying elasticity and/or hardness parameters of the tissue. Also, the signals can be echographic data detected with an acoustic sensor. Besides, the signals can be optic data detected with an optical sensor. After acquisition of data of one single plane, the sensor can be moved to acquire data in another plane (which, for example, is parallel to the previous plane) to assess deformation of tissue in more than one image plane. The signals, at an assumed cyclic pressure change, can also be received at predetermined time intervals in the period of motion. The signals may come from a blood vessel wall and that the data are received only during a specific time interval of the period of the heartbeat. Data can be acquired in certain parts of the heart cycle using the ECG or using a device to measure the pulsatile blood pressure in the tissue under investigation or another tissue or tissue structure than the tissue or tissue structure under investigation.

Besides, as follows from the above, an apparatus for generating hardness and/or strain information of tissue, which tissue can be subject to a varying pressure, can comprise:

a sensor capable of generating and receiving measuring beams or signals with different angles towards the sensor surface, wherein the sensor preferably includes at least one transducer, preferably a linear array transducer.

a beam steering device to control the way in which the measuring beams are generated and received by the sensor.

a processor device for collecting and processing signals received by the sensor to identify strain of the tissue and to relate the strain to elasticity and/or hardness parameters of the tissue.

a display device for displaying said elasticity and/or hardness parameters of the tissue.

a position recording device coupled with the processor device to record sensor positions The apparatus can further comprise an actuator for moving the sensor. Besides, the apparatus can further comprise an activating means or activator for activating the actuator. Also, in this case, the activating means can be connected to an ECG recording device and/or pressure monitoring device to become active during a predetermined part of the heartcycle. As an example, the sensor can be an acoustic sensor, or an optical sensor It is to be understood that in the present application, the term "comprising" does not exclude other elements or steps. Also, each of the terms "a" and "an" does not exclude a plurality. Any reference sign(s) in the claims shall not be construed as limiting the scope of the claims. Also, a single processor, controller or other unit may fulfil functions of several means recited in the claims.

Although the invention has been discussed on the basis of the above mentioned exemplary embodiments, it is clear that the invention can also be used when detecting and analyzing other tissues, such as (for cancer research of) the prostate, the esophagus, the cervix etc. Such and other variations are deemed to be within reach and the scope of protection of the appended claims.

For example, in the embodiments of FIGS. 1 and 2, said transducer surface is a substantially flat surface, and the transducer surface is faced toward the location of the tissue to be investigated. However, the transducer surface can also be shaped.

In the present application, the term "tissue" should be interpreted broadly, as will be clear to the skilled person. Particularly, the tissue can be part of a human or animal body.

Besides, said transducer, signal transmitter signal receiver or transducer can be arranged and constructed in various ways, as will be clear to the skilled person. Preferably, the signal transmitter and signal receiver are located at the same side of a tissue to be investigated. This can be the case, for example, when the signal transmitter and signal receiver are provided by an acoustic transducer. Besides, a plurality of sensors, transducers, signal transmitters and/or signal receivers can be utilized.

The invention claimed is:

1. A method for generating hardness and/or strain information of a wall of a blood vessel, having a substantially circular cross-section, the blood vessel subject to a pressure cycle caused by varying pressure induced by a heartbeat, to determine deformation of the blood vessel wall, the method comprising:

positioning at least one signal transmitter outside the blood vessel wall so that emitted signals therefrom encompass a transverse contour of the blood vessel;

positioning at least one signal receiver outside the blood vessel wall;

using the signal transmitter in a first step and a second step to emit signals (S) towards the blood vessel wall at a different angle in each step with respect to the transmitter's emitting surface viewed in the transverse cross-section of the blood vessel, wherein emitting signals (S) in each of the first step and the second step includes emission of a plurality of signals that encompass the contour of said blood vessel wall while the blood vessel is at various levels of deformation due to heart beat induced internal pressure variations, wherein the deformation of the blood vessel is not caused by external compression;

using the signal receiver to receive reflected or partly reflected signals from the blood vessel wall in each step, wherein the received signals result from the signals that have been emitted by said signal transmitter;

acquiring strain image data from the received signals in the first step and the second step, wherein in each step a strain image can be acquired for regions where no strain image can be obtained for in another step; and compounding the image data acquired from received signals in the first step and the second step for full reconstruction of the radial and circumferential strain for all regions of the blood vessel wall, and relating the strain of the blood vessel wall to elasticity and hardness parameters of the blood vessel wall;

wherein said transmitter and/or said receiver is substantially not moved with respect to the blood vessel wall during the emitting and receiving of said signals; and wherein the emitted signals (S) have a direction that substantially is not aligned with a direction of internal blood pressure induced radial strain in the blood vessel wall.

2. A method according to claim 1, wherein the signal transmitter subsequently sends signals (S) towards the blood vessel wall in at least a first and a second measuring plane corresponding the first step and the second step respectively, wherein the first measuring plane (P1) intersects the blood vessel wall with a different angle than the second measuring plane (P2), wherein each sending of the plurality of signals in a measuring plane is composed of sending signals towards the blood vessel wall while the blood vessel wall is at different levels of deformation.

3. A method according to claim 2, further comprising measuring the deformation of the blood vessel wall in each measuring plane defined by the transmitter and/or receiver, in which plane the emitted signals are all substantially parallel.

4. A method according to claim 2, wherein said angles in the first step and the second step differ in the range of 25-65 degrees.

5. A method according to claim 1, wherein said angles in the first step and the second step differ in the range of 25-65 degrees.

6. A method according to claim 1, wherein said transmitter and said receiver are provided by at least one of a signal transducer and a linear array transducer.

7. A method according to claim 1, wherein said emitted signals are acoustic signals.

8. A method according to claim 1, characterized in that the emitted signals are optical signals.

9. A method according to claim 1, wherein the signals received from the blood vessel walls are received in a first and a second image planes; and further comprising moving the transmitter and/or receiver to another location to acquire data in another plane in order to examine different parts of the blood vessel wall.

10. A method according to claim 1, characterized in that the signals, at an assumed or predetermined cyclic pressure change of said blood vessel wall, are received at predetermined time intervals in a period of motion.

11. A method according to claim 1, wherein said signals are being sent and received during a specific time interval of a period of a respective heartbeat.

12. A method according to claim 1, characterized in that said signals are used to acquire data in certain parts of a heart cycle using an ECG or using a device to measure pulsatile blood pressure in the blood vessel wall or blood vessel wall part under investigation or a blood vessel wall or blood vessel wall part other than the blood vessel wall or blood vessel wall part under investigation.

13. A method for generating hardness and/or strain information of a wall of a blood vessel, having a substantially circular cross-section, the blood vessel subject to a pressure cycle caused by varying pressure induced by a heartbeat, to determine deformation of the blood vessel wall, the method comprising:

positioning at least one signal transmitter outside the blood vessel wall so that emitted signals therefrom encompass a transverse contour of the blood vessel;

positioning at least one signal receiver outside the blood vessel wall;

using the signal transmitter, in each of in a first step and a second step, to emit diverging signals (S) towards the blood vessel wall, from a different location on the transmitter's emitting surface in each step, while the blood vessel is at various levels of deformation due to heart beat induced internal pressure variations, wherein the deformation of the blood vessel is not caused by external compression;

acquiring strain image data from the received signals in the first step and the second step, wherein in each step a strain image can be acquired for regions where no strain image can be obtained for in another step; and compounding the image data acquired from received signals in the first step and the second step for full reconstruction of the radial and circumferential strain for all regions of the blood vessel wall, and relating the strain of the blood vessel wall to elasticity and hardness parameters of the blood vessel wall;

wherein said transmitter and/or said receiver is substantially not moved with respect to the blood vessel wall during the emitting and receiving of said signals; and wherein the emitted signals (S) have a direction that substantially is not aligned with a direction of internal blood pressure induced radial strain in the blood vessel wall.

* * * * *

UNITED STATES PATENT AND TRADEMARK OFFICE
CERTIFICATE OF CORRECTION

PATENT NO. : 8,617,074 B2  Page 1 of 1
APPLICATION NO. : 11/990543
DATED : December 31, 2013
INVENTOR(S) : Christoffel Leendert De Korte

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 916 days.

Signed and Sealed this
Twenty-second Day of September, 2015

Michelle K. Lee
*Director of the United States Patent and Trademark Office*